(12) United States Patent
Hellstrom et al.

(10) Patent No.: US 10,357,661 B2
(45) Date of Patent: Jul. 23, 2019

(54) MEDICAL DEVICE AND METHOD FOR INTERNAL HEALING AND ANTIMICROBIAL PURPOSES

(71) Applicants: Ake A. Hellstrom, Columbus, OH (US); Errol O. Singh, Columbus, OH (US)

(72) Inventors: Ake A. Hellstrom, Columbus, OH (US); Errol O. Singh, Columbus, OH (US); Allen Stock, Columbus, OH (US)

(73) Assignee: PERCUVISION, LLC, Westerville, OH (US)

( * ) Notice: Subject to any disclaimer, the term of this patent is extended or adjusted under 35 U.S.C. 154(b) by 683 days.

(21) Appl. No.: 14/348,088

(22) PCT Filed: Sep. 28, 2012

(86) PCT No.: PCT/US2012/057800
§ 371 (c)(1),
(2) Date: Mar. 28, 2014

(87) PCT Pub. No.: WO2013/049491
PCT Pub. Date: Apr. 4, 2013

(65) Prior Publication Data
US 2014/0235942 A1     Aug. 21, 2014

Related U.S. Application Data

(60) Provisional application No. 61/542,123, filed on Sep. 30, 2011.

(51) Int. Cl.
*A61N 5/06* (2006.01)
*A61B 1/00* (2006.01)
(Continued)

(52) U.S. Cl.
CPC ........ *A61N 5/0603* (2013.01); *A61B 1/00071* (2013.01); *A61B 1/00091* (2013.01);
(Continued)

(58) Field of Classification Search
CPC ........... A61B 1/06; A61B 1/0615; A61B 6/08; A61N 2005/063; A61N 2005/0652; A61N 5/0601; A61N 5/0624
See application file for complete search history.

(56) References Cited

U.S. PATENT DOCUMENTS

| 4,248,214 A | 2/1981 | Hannah et al. |
| 4,754,752 A | 7/1988 | Ginsburg et al. |

(Continued)

FOREIGN PATENT DOCUMENTS

| CN | 101002698 A | 7/2007 |
| CN | 201135707 Y | 10/2008 |

(Continued)

*Primary Examiner* — Deanna K Hall
(74) *Attorney, Agent, or Firm* — Standley Law Group LLP; Jeffrey S. Standley; Jeffrey C. Norris

(57) ABSTRACT

Process and device for directly medicinally treating interior tissue during or after intubation of a patient by passing medicinal radiant energy transversely through the intubation device to irradiate the internal patient tissue for promoting healing or for an antimicrobial effect. The invention is useful in conjunction with endoscopies and catherizations, such as urinary catherization, gastric and pulmonary endoscopies, and the like procedures. The process and device can also provide liquid flow and/or vision.

8 Claims, 9 Drawing Sheets

(51) Int. Cl.
*A61B 1/015* (2006.01)
*A61B 1/06* (2006.01)
*A61B 1/05* (2006.01)
*A61B 1/233* (2006.01)
*A61B 1/267* (2006.01)
*A61B 1/273* (2006.01)
*A61B 1/303* (2006.01)
*A61B 1/31* (2006.01)
*A61B 1/313* (2006.01)
*A61B 1/317* (2006.01)
*A61B 17/00* (2006.01)
*A61M 16/04* (2006.01)
*A61M 25/00* (2006.01)
*A61N 5/067* (2006.01)

(52) U.S. Cl.
CPC .............. *A61B 1/015* (2013.01); *A61B 1/05* (2013.01); *A61B 1/06* (2013.01); *A61B 1/0615* (2013.01); *A61B 1/233* (2013.01); *A61B 1/2676* (2013.01); *A61B 1/273* (2013.01); *A61B 1/303* (2013.01); *A61B 1/31* (2013.01); *A61B 1/317* (2013.01); *A61B 1/3132* (2013.01); *A61B 17/00234* (2013.01); *A61M 16/0488* (2013.01); *A61M 25/0023* (2013.01); *A61N 5/0601* (2013.01); *A61N 5/0624* (2013.01); *A61M 2025/0004* (2013.01); *A61N 2005/061* (2013.01); *A61N 2005/063* (2013.01); *A61N 2005/067* (2013.01); *A61N 2005/0609* (2013.01); *A61N 2005/0651* (2013.01); *A61N 2005/0652* (2013.01); *A61N 2005/0653* (2013.01); *A61N 2005/0659* (2013.01); *A61N 2005/0661* (2013.01); *A61N 2005/0662* (2013.01)

(56) References Cited

U.S. PATENT DOCUMENTS

| | | | |
|---|---|---|---|
| 5,281,212 A | 1/1994 | Savage et al. | |
| 5,320,617 A | 6/1994 | Leach | |
| 5,454,794 A | 10/1995 | Narciso et al. | |
| 5,593,404 A | 1/1997 | Costello et al. | |
| 6,013,053 A | 1/2000 | Bower et al. | |
| 6,086,558 A | 7/2000 | Bower et al. | |
| 6,146,409 A | 11/2000 | Overholt et al. | |
| 6,551,346 B2 | 4/2003 | Crossley | |
| 6,616,653 B2 | 9/2003 | Beyar et al. | |
| 6,962,584 B1 | 11/2005 | Stone et al. | |
| 6,986,764 B2 * | 1/2006 | Davenport ............ | A61B 18/22 600/2 |
| 7,018,397 B2 | 3/2006 | Neuberger | |
| 7,041,121 B1 | 5/2006 | Williams et al. | |
| 7,305,163 B2 | 12/2007 | Williams | |
| 7,526,344 B2 | 4/2009 | Kim | |
| 7,763,058 B2 | 7/2010 | Sterenborg et al. | |
| 7,883,503 B2 | 2/2011 | Kaiser et al. | |
| 7,955,365 B2 | 6/2011 | Doty | |
| 2002/0087206 A1 | 7/2002 | Hirschberg et al. | |
| 2002/0193850 A1* | 12/2002 | Selman ............... | A61N 5/02 607/89 |
| 2003/0171795 A1 | 9/2003 | Walmsley et al. | |
| 2005/0019256 A1 | 1/2005 | Dobkine et al. | |
| 2006/0195165 A1 | 8/2006 | Gertner et al. | |
| 2006/0224169 A1 | 10/2006 | Weisenburgh, II et al. | |
| 2007/0135874 A1 | 6/2007 | Bala | |
| 2007/0260295 A1 | 11/2007 | Chen et al. | |
| 2008/0015661 A1 | 1/2008 | Friedman et al. | |
| 2008/0027416 A1 | 1/2008 | Hamel et al. | |
| 2008/0015990 A1 | 7/2008 | Redmond | |
| 2008/0208297 A1 | 8/2008 | Gertner et al. | |
| 2008/0221458 A1 | 9/2008 | Scott et al. | |
| 2008/0306454 A1 | 12/2008 | Sikora | |
| 2009/0216300 A1 | 8/2009 | Keltner et al. | |
| 2009/0318816 A1 | 12/2009 | Knighton et al. | |
| 2009/0319008 A1 | 12/2009 | Mayer | |
| 2010/0016844 A1 | 1/2010 | Patel, Jr. | |
| 2010/0145415 A1 | 6/2010 | Dahm et al. | |
| 2010/0179523 A1 | 7/2010 | Neuberger et al. | |
| 2010/0274330 A1 | 10/2010 | Burwell et al. | |
| 2011/0040170 A1 | 2/2011 | Geva et al. | |
| 2011/0060388 A1 | 3/2011 | Neuberger | |
| 2011/0077464 A1 | 3/2011 | Burwell et al. | |
| 2011/0118547 A1 | 5/2011 | Erikawa | |
| 2011/0190747 A1 | 8/2011 | Derbin et al. | |
| 2011/0190748 A1 | 8/2011 | Donaghy et al. | |

FOREIGN PATENT DOCUMENTS

| | | |
|---|---|---|
| DE | 10239950 B3 | 2/2004 |
| DE | 102006039471 B3 | 3/2008 |
| JP | 2006055337 A | 3/2006 |
| WO | WO03/02013 A2 | 3/2003 |
| WO | WO2006/081312 A2 | 8/2006 |
| WO | WO2006/121407 A1 | 11/2006 |
| WO | WO2007/084608 A2 | 7/2007 |
| WO | WO2007/109496 A2 | 9/2007 |
| WO | WO2008/136958 A1 | 11/2008 |
| WO | WO2009/019710 A2 | 2/2009 |
| WO | WO2009/125338 A1 | 10/2009 |
| WO | WO2010/029292 A1 | 3/2010 |
| WO | WO2010/118333 A2 | 10/2010 |
| WO | WO2010/132429 A2 | 11/2010 |
| WO | WO2011/020064 A2 | 2/2011 |
| WO | WO2011/055395 A1 | 5/2011 |
| WO | WO2011/094541 A1 | 8/2011 |

* cited by examiner

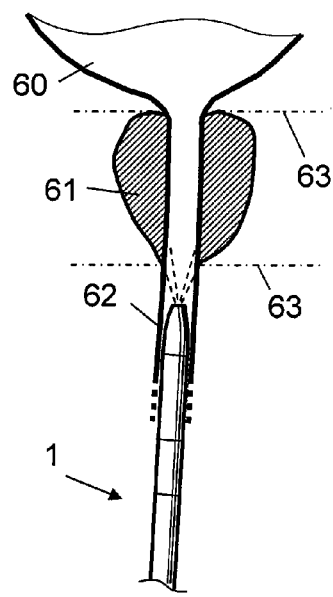 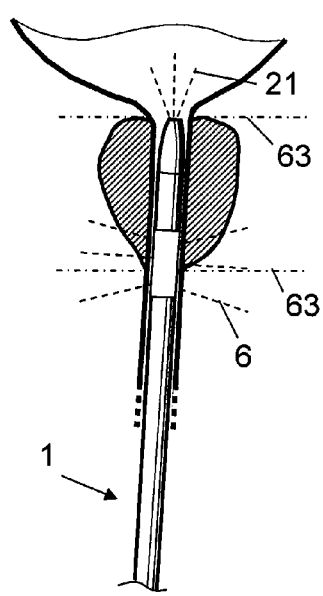 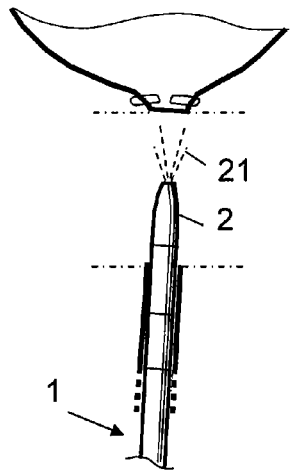
Figure 12a   Figure 12b   Figure 12c
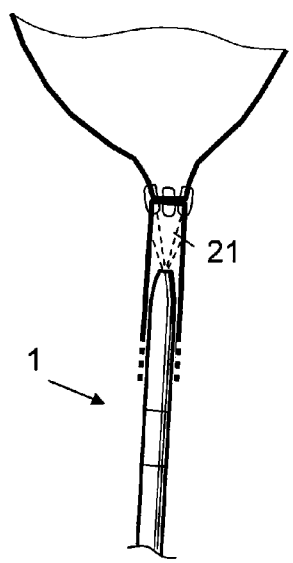 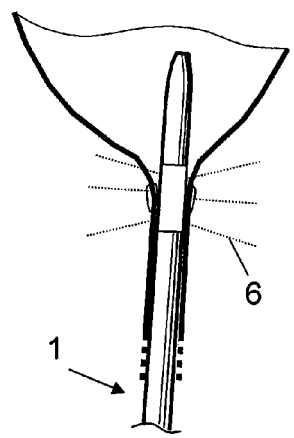 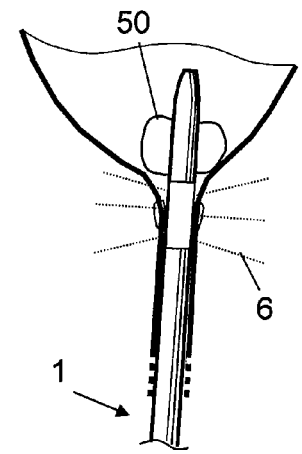
Figure 12d   Figure 12e   Figure 12f

MEDICAL DEVICE AND METHOD FOR INTERNAL HEALING AND ANTIMICROBIAL PURPOSES

CROSS-REFERENCE TO RELATED APPLICATIONS

This is a National Phase Application filed under 35 U.S.C. 371 as a national stage of PCT/us2012/057800, filed on Sep. 28, 2012, claiming the benefit under 35 U.S.C. 119(e) of U.S. Provisional Application No. 61/542,123, filed on Sep. 30, 2011, the content of each of which is hereby incorporated by reference in its entirety.

BACKGROUND OF THE INVENTION

This invention is in the technical field of medical instruments and involves fluid handling, light treatment for internal healing, antimicrobial features and vision; and it is exemplified by catheters for urology. As one example of applications, a catheter according to the invention may be utilized during and after radical prostatectomy or urethral reconstruction to promote faster healing and improve general outcome of the procedure. As another example of applications, a catheter according to the invention may be in-dwelling for an extended time in patients while providing reduced risk for infections that may otherwise arise with long term use. Additional applications of the invention include other medical fields that utilize catheters, endoscopes or similar instruments internally in the patient.

The use of catheters inside the body is necessary for several medical conditions and procedures—with associated risks. As an example, it has been suggested that urinary tract infections today contribute to approximately 40% of hospital acquired infections. The infection risk accelerates with longer in-dwelling time. This is a significant issue for the patient long term health and quality of life, and a non-trivial part of the problematic national healthcare cost situation. Various methods have been suggested for catheters to achieve reduced infection risk. This includes for instance, improved antimicrobial coatings, materials with low affinity for harboring foreign matter, agents applied at time of use on the catheter exterior, as well as catheter insertion shields and protection methods.

But despite all this available catheter technology, the current rate of urinary tract infections related to urology procedures is still a major problem. One option is to apply higher doses, more potent or new formula antimicrobial agents. This may not be a viable solution for the future due to breeding of resistant microbial strains. General concerns in all methods that apply antimicrobial agents onto catheters include quality control of the initial application for adequate coverage, and the potential risk for agent removal or degradation by extended time of use, or by catheter to patient motion. The effectiveness of the antimicrobial application is therefore uncertain for long term use. The exterior of the catheter may be touched by the patient's hands or nearby body parts which may harbor bacteria. As an example, the female anatomy introduces a special risk by the proximity between the urethral meatus to the vaginal vault and also the anus. There is additionally a risk of infection through the liquid carrying lumen internal of the catheter. Although the urine is generally sterile and flows away from the patient, bacteria may enter the urinary system through a catheter lumen due to position changes and of catheter and patient and gravity, or by slow migration and liquid turbulence.

One example of a major urology procedure is radical prostatectomy. This has recently been improved with advanced instruments for robot assisted laparoscopic surgery. As part of this procedure, the severed urethra has to undergo anastomosis to the urethral stump at the bladder. It is essential that the healing process for the urethra is starting under favorable conditions and as early as possible, for faster recovery, patient comfort and reduced risk for scars or strictures as added complications later on. Furthermore, the urethra/bladder must be significantly stretched in length for anastomosis after the prostate removal and can not be stretched any further, so a repeat operation is not viable. This implies that doing the anastomosis procedure right the first time is essential. Particular problems to be solved include better visualization and control of the anastomosis for the operator, and methods to achieve a head start of the healing process at an early stage for quicker recovery and less scar tissue. This can also assist in reducing the length of time for the patient to stay catheterized as part of post-surgery. The catherization is currently approximately 7-14 days depending on healing progress and surgery quality, and such a lengthy in-dwelling period also may increase risk for urinary tract infections related to the catheter.

Catheters that provide integrated vision devices in addition to liquid handling have been introduced. A real time view of the interior of body lumina and cavities during catherization significantly reduces the risk for mis-catherization. To implement this for urology procedures was a particular challenge for the small diameter, highly flexible catheters that are demanded for urology. It has recently resulted in successful commercial products. Such vision catheters are described in U.S. Pat. Nos. 6,994,667 and 6,599,237, and also in PCT patent application PCT/US12/40877, filed Jun. 5, 2012, all of which are hereby incorporated by reference.

Due to the recently improved understanding of light interaction with living cells, low level light therapy in the medical field has received new attention. There is an increasing use of low level light radiation as a means of sterilizing, antimicrobial, stimulating or healing function in medical devices and procedures. Such applications were first focused on external treatment but are now also finding use inside body cavities, lumina and openings created by surgical procedures. Applications of light energy in urology have so far been limited to diagnostics, high energy treatment for localized heating or by killing undesired cells by vaporization, or light for photodynamic therapy by activating drugs or other agents at desired location in the patient.

For applications like urology, the cross-sectional area of catheters is limited due to the confines of the urethra. This has been a barrier in making a catheter with light treatment functionality as well as liquid handling. It is obvious that the problem is even more difficult to solve to include both vision and light treatment capability to a small size fluid handling catheter.

Another limiting factor in catheters borne by a patient for extended time is the convenience and comfort for the patient to move around and to perform normal personal duties. Catheters that are long term in-dwelling should ideally be light weight, flexible, compact and have no need for cables to a stationary apparatus.

Although the examples recited in this invention are primarily related to catheterization in urology, there are similar needs in several other medical fields where the invention can assist to solve current problems. Examples of such fields of use include but are not limited to: endotrachial, pulmonology, gynecology, proctology, cardiology, gastric including oral or nasogastric intubation, and vascular surgery or treatment.

It is additionally noted that the term "catheter with vision" may be overlapping in function with terms similar to "endoscope including fluid handling." This invention may therefore also be applied for problem solving in applicable fields of endoscopy with fluid handling. Specialty endoscopy applications for the invention may include, but are not limited to, laparoscopy, bronchoscopy, gynoscopy, rhinoscopy, arthroscopy, enteroscopy and colonoscopy.

It is the goal of this invention to provide a catheter platform system that overcomes the mentioned difficulties of prior art. In addition it has low cost, it is disposable and can be adapted to both male and female patients and tailored for specific needs.

SUMMARY OF THE INVENTION

The present invention defines catheter platform for urology use and other medical applications, where the catheter includes fluid channels and integrated illumination from light source(s) for healing and/or antimicrobial action.

In another aspect, the invention defines a catheter for urology use and other medical applications, were the catheter includes fluid channels, vision device(s), and integrated illumination from light source(s) for healing and/or antimicrobial action.

In a first embodiment of the invention, the catheter includes an external translucent sleeve and a translucent inner tube assembly inside this sleeve, where the tube assembly is insertable and removable from the sleeve through the proximal end of the sleeve, and serves as housing for light sources for healing treatment and/or antimicrobial features.

In another aspect of the first embodiment of the invention, the external diameter of the inner tube assembly is less than the internal diameter of the sleeve, permitting an annular shape first fluid channel in the space between the tube and the sleeve.

In yet another aspect of the first embodiment, the sources for light treatment or antimicrobial action and associated electrical wiring inside the tube assembly are coated with a thin translucent layer permitting light transmission and heat transfer to liquid or air, while providing electric insulation such that the interior of the inner tube may be utilized as a second fluid channel.

In yet another aspect of the first embodiment, the sources for light treatment or antimicrobial action are thin profile LEDs or laser diodes that may be mounted back to back in pairs at 180 degrees and at 90 degrees alternating angles between pairs to provide a generally 360 degree coverage radial illumination inside the body lumen or cavity.

In yet another aspect of the first embodiment, the first fluid channel may be used for fluid drain from the patient, and the second fluid channel for irrigation or medication to the patient, while the irrigation flow may also serve as coolant for the treatment light sources and return through the first fluid channel. Any flow in the catheter may also have different purposes or in reversed direction if so demanded.

In another aspect, a vision device is present in the catheter in addition to fluid handling and light treatment or antimicrobial light.

In yet another aspect of the first embodiment, the vision device is a camera attached near the distal end of the inner tube assembly.

In yet another aspect of the first embodiment, the vision device is a fiber optics imaging system attached near the distal end of the inner tube assembly In a second embodiment of the invention, the catheter the inner tube includes internally longitudinal fiber optics bundle for coupling of remote light sources to provide light for treatment or antimicrobial features of the catheter.

In another aspect of the second embodiment, the longitudinal fiber optics members for light treatment or antimicrobial light are bent towards the radial direction at their distal ends and arranged to provide 360 degree radial light treatment illumination or antimicrobial action inside the body lumen or cavity and catheter fluid channels.

In another aspect of the second embodiment, a vision device can be present in the catheter in addition to fiber optics bundle for treatment or antimicrobial light.

In yet another aspect of the second embodiment, the vision device is a camera.

In yet another aspect of the second embodiment, the vision device is fiber optics coupled remote imaging.

In one aspect of either embodiment, treatment light sources are selected with wavelengths, energy level and pulsing schemes in order to assist healing the patient's tissue from inside the body lumen or cavity.

In yet another aspect of either embodiment, antimicrobial light sources are selected with wavelengths, energy level and pulsing schemes in order to achieve antimicrobial action on the catheter exterior, on the inside walls of the patient's body lumen or cavity and the content of fluid channels in the catheter.

In yet another aspect of either embodiment, both the light sources for healing treatment and light sources for antimicrobial action are present in the catheter and illuminate separate areas or a common area.

Therefore, in accordance with the present invention, there is provided a process for medicinally treating interior tissue of a patient during or after an intubation of the patient, along with the passage of a fluid to or from the patient, by intubating the patient for accessing the interior tissue of the patient to be medicinally treated using an intubation device having both an interior lumen within an exterior sleeve and a fluid channel within the exterior sleeve, and during and/or after the intubation, passing medicinal radiant energy, in a dose effective for providing a direct medicinal benefit to the treated tissue, from the interior lumen transversely through the exterior sleeve of the intubation device to irradiate the interior tissue, and passing a fluid to or from the patient through the fluid channel. In a preferred embodiment of the present invention, the medicinal radiant energy, is provided to the treated interior tissue in a dose effective for promoting the healing of the tissue and/or for providing an antimicrobial effect to the intubation device, fluids in the intubation device and/or to the patient tissue.

Also, in accordance with the present invention, there is provided a catheter having an outer translucent sleeve through which medicinal radiant energy can pass, having a vision and illumination device positioned at its distal end, having a translucent tube positioned within the sleeve, which is insertable and removable from the outer sleeve proximal end and carries at least one radiant energy source capable of transmitting medicinal radiant energy transversely through both the translucent tube and the translucent sleeve into the interior of the patient for treating interior tissue of the patient, and having a fluid channel for passing a fluid to or from the patient and formed by the space between the tube and the sleeve. In a preferred embodiment of this invention, the radiant energy source emits medicinal radiant energy in a dose effective for providing a direct medicinal benefit to the interior treated tissue of the patient. In a more preferred embodiment of this invention, the emitted medicinal radiant energy is provided in a dose effective for directly promoting healing of or providing an antimicrobial effect to the intubation device, fluids in the intubation device and/or to treated interior tissue.

The following aspects of the invention describe an example of clinical use of the invention catheter for radical prostatectomy; however, the invention may also be utilized for other medical procedures with similar needs for fluid handling, light treatment and vision.

In one aspect of clinical use of the invention, it is favorably applied to improve the outcome, shorten patient recovery time and reduce risks of the radical prostatectomy.

In a prostatectomy procedure utilizing the invention, as a first sequential step, a catheter with treatment light sources and vision device is utilized to internally illuminate the prostate and bladder area for surgery creating externally visible illumination from the catheter through the thin urethra or bladder walls, while additionally also imaging the interior of the urethra and bladder.

In another aspect of the invention applied to prostatectomy, as a next sequential step of utilization, a catheter with treatment light sources and vision is applied after prostate gland removal to aid in illumination and inspection from inside of the urethra, and as an aid in suturing the urethra to the bladder urethral stump for assisting the operator in achieving an accurate anastomosis.

In yet another aspect of the invention applied to prostatectomy, the catheter tip at the distal end has a hard surface to prevent urethral suturing to falsely attach to the catheter in an anastomosis procedure.

In yet another aspect of the invention, as a next sequential step the catheter is utilized to inspect the result of the anastomosis from the inside of the urethra.

In yet another aspect of the invention applied to prostatectomy, as a next sequential step the catheter treatment lighted area is aligned with the anastomosis area and energized to start light stimulated healing after suturing is completed and remain activated as long as needed to assist optimum healing of the anastomosis wound.

For a different aspect of clinical use of the invention, the catheter treatment light sources are utilized to promote healing after a urethral reconstruction procedure.

In yet a different clinical use aspect of the invention, the illumination from the treatment light sources is directed onto the interior of the patient lumen or cavities for the purpose of treating diseased areas with light.

As a yet another aspect of clinical use of the invention, it is applicable for antimicrobial treatment during catheterization of extended duration to reduce infection risks associated with long in-dwelling time of a catheter. The invention catheter in this aspect assists to reduce infection risk by illumination from integrated light sources selected for antimicrobial action while not harming the patient.

In one aspect of clinical use of the invention, the antimicrobial treatment light is radiated around the catheter at the point of catheter entry into the patient and the interior of the patient body lumen, in order to create a light barrier that will kill bacteria that may attempt to migrate into the patient through the narrow passage between the catheter exterior and the lumen interior, and to reduce chance for biofilm buildup on the catheter surface.

In another aspect of the clinical use of invention, the antimicrobial treatment light sources illuminate the fluid channels internal of the catheter in such a way that any matter or bacteria that attempt to migrate in the direction in to the patient body through the fluid channels of the catheter is antimicrobial treated by illumination from the light sources.

In one clinical aspect of the invention, the illumination zone from the light treatment antimicrobial sources includes the urethral meatus location in order to create a barrier at the point of possible entry of infections matter.

In yet another aspect of the invention, the antimicrobial and light treatment illumination zones are localized at certain points of the catheter length for the urinary tract anatomy in a way suitable to a male patient.

In yet another aspect of the invention, the antimicrobial and light treatment illumination zones are localized at certain points of the catheter length for the urinary tract anatomy in a way suitable to a female patient.

In yet another aspect of the invention, the catheter longitudinal direction location of illumination zones to the patient can be adjusted by moving the inner tube assembly longitudinally versus the sleeve.

In yet another aspect of the catheter, the light sources for healing and antimicrobial action are powered by an electric energy source included with the catheter.

In yet another aspect of the catheter, the electric energy source circuit with a battery is mounted near the proximal end of the catheter, preferably at the catheter manifold.

In accordance with the present invention, the radiant energy will be applied to the internal tissue in type of radiant energy and at a power and accumulated dose for accomplishing the desired objective with positive treatment results and without harming the patient. Wavelengths may be in the range 450-1000 nm for healing treatment and 350-600 nm for antimicrobial action. For example, the practitioner could select the use of red light radiant energy, which passes easily through body tissue, for alleviation of below tissue surface inflammation, or select the use of blue or UV light, which mainly affects the tissue surface, for an antimicrobial effect along the outer cells of the internal tissue. As a general guideline, the peak power of the radiant energy (irradiance) will be within the range of about 0.1 to about 200 milliwatts per square centimeter ($mW/cm^2$), preferably about 0.1 to about 20 $mW/cm^2$. As another guideline, the integrated total patient exposure energy density could be within the range of about 0.01 to about 50 $J/cm^2$, preferably about 0.1 to about 10 $J/cm^2$. For example, if the peak irradiance is 1 $mW/cm^2$ and total on time for all light pulses to the patient is 100 seconds, the administered energy density will be 0.1 $J/cm^2$. It is noted that short wavelength light like UV can be additionally restricted in lower power and energy levels compared to long wavelengths, due to significantly higher cell sensitivity for short wavelength radiation.

In yet another aspect of the catheter, the light sources for healing treatment and antimicrobial action are modulated by a pulsing sequence optimized for the duration of patient urology treatment in order to maximize treatment and antimicrobial effects, keeping the total light dose within prescribed safe limits, and save battery power.

In yet another aspect of the invention, the catheter includes a method for monitoring the healing light process or antimicrobial light process by a sensor in the catheter, for instance a temperature sensor, and giving an alarm if conditions warrant.

In yet another aspect of the invention, the catheter sleeve and inner tube assembly are both disposable.

In yet another aspect of the invention, the catheter sleeve is disposable while the inner tube assembly is reusable.

BRIEF DESCRIPTION OF THE DRAWINGS

FIGS. 12a through 12f shows a schematic representation of the sequential steps of utilization of the catheter system for radical prostatectomy surgery.

DETAILED DESCRIPTION OF THE INVENTION

Figure 1:
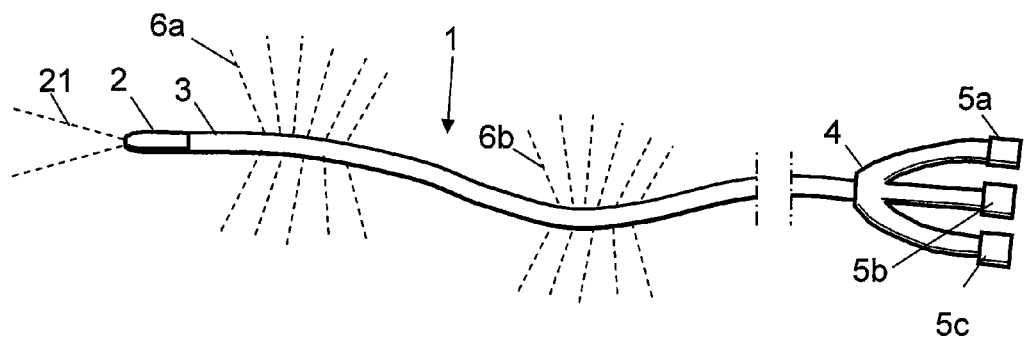
FIG. 1 shows a side view of the catheter exterior in one implementation, including fluid handling, healing light illumination and vision.

This invention is about a catheter platform system using low level light energy to improve healing, and to reduce infection risk in a wide range of internal medical conditions and procedures. In the description there are references to mainly urology procedures but it is emphasized that the invention is equally applicable to many other medical procedures and treatment of conditions inside vessels and cavities of human or animal bodies. In the description there is also a reference to energy sources as "light sources" but this includes visible, UV or IR wavelengths, and other electromagnetic radiation, and may be monochromatic, broad band, or simultaneous or alternating multiple wavelengths by a combination of different type of sources. Light sources may furthermore utilize LEDs, lasers, flash lamps, incandescent or gas discharge lamps, or OLEDs. Light beam geometry from light sources may be narrow, wide or diffuse. The light sources they may be integrated inside the catheter if available in small dimensions or remote/fiber coupled to create one or more virtual light sources at point of use. Light sources may be continuously enabled or pulsed in schemes that enhance treatment effect and reduce power consumption and heat dissipation.

The basic goal of this invention is to provide a catheter platform system that as a minimum serves the dual purpose of providing fluid channels as well as light energy for healing, treatment or antimicrobial action. The invention can also simultaneously utilize previously described vision systems for a catheter, providing additional benefits.

In order to include three simultaneous functions—fluid handling, vision, and light treatment such as an antimicrobial light feature—in one catheter, creates a very difficult design challenge for small diameter catheters as needed by for example urology. Additionally, the demand for improved patient outcome, while also achieving cost reduction of the medical treatment in general, and cost control for medical equipment adds additional design burdens. The invention presents novel solutions that are believed to meet all these needs without major conflicts.

The low level light treatment applications of this invention fall in basically two groups:

light treatment for healing after surgery or for treating medical conditions antimicrobial light to kill bacteria or other infectious matter, for instance to reduce infection risk from extended in-dwelling time catherization Light treatment for healing after surgery is exemplified by an application of the catheter system for radical prostatectomy procedures. In this application, the catheter system will assist to improve the anastomosis of the severed urethra by application of healing light energy from the urethra interior soon after the anastomosis. As a side benefit, the catheter platform may also be utilized during several other steps of the procedure to better visualize the surgery area, which is especially beneficial in a laparoscopic procedure. However, the invention can also be applied to other urology procedures like urethral reconstruction, stricture treatment, curing inflammations and more. Additionally, it may be beneficially utilized inside any body vessels or body cavities to assist in improved anastomosis results, and for other internal healing or medical condition treatment.

For antimicrobial treatment with the invention, this is exemplified by long term urethral catherization of male or female patients. In this application, the action of light in the catheter creates an antimicrobial barrier to reduce risk of spreading bacteria from the external ambient via the catheter into the patient with the ultimate goal of preventing urinary tract infections. In a preferred embodiment, simultaneous healing action and antimicrobial action is obtained from the emitted radiant energy.

It shall also be pointed out that the invention defines a novel catheter platform that includes several novel features or subsystems, and can be applied by novel processes. The description offers a few examples of processes, subsystems, features and embodiment; but all possible combinations and permutations of processes, features or subsystems of the invention can not described in detail due to need to control document growth. Therefore, catheter platform systems that utilize any other combination or permutations of processes, features or subsystems as described in the specification are hereby considered as additional implementations under this invention.

The invention is now described by explaining each of the drawn figures in detail.

FIG. 1 shows a side view of the exterior of a catheter according to the invention. The catheter 1 consists of a sleeve 3, a tip 2 at the distal end that will be inserted in the patient, and a fluid handling manifold 4 at the proximal end with associated fluid or accessory fittings 5a, 5b and 5c, which may vary by quantity and type of fittings, as known by prior art. The tip 2 may be straight or set at an angle, the latter for navigation through curved body vessels. The catheter 1 emits low level light energy 6 for healing, treatment or antimicrobial purposes through the sleeve 3 in generally radial directions. The catheter 1 may have one or multiple light emission locations in the length direction of the catheter exemplified by light energy 6a and 6b. The catheter 1 has optionally also a vision system at the distal end with a generally axial field of view 21, also including generally axial vision and illumination and/or treatment energy, which is disclosed by the referenced PCT patent application PCT/US12/40877. The catheter 1 is preferably manufactured of translucent materials, as a minimum at the locations of light energy 6a and 6b.

Figure 2:
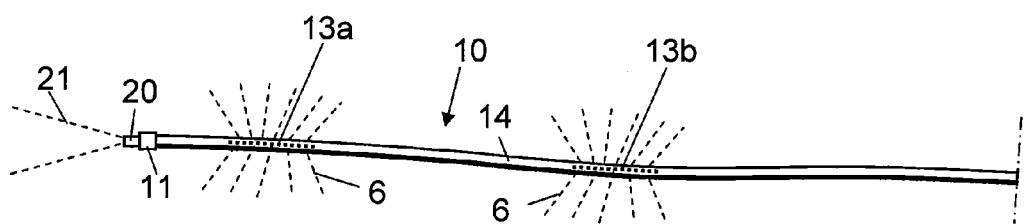
FIG. 2 shows a side view of the removable inner tube assembly of the catheter.

FIG. 2 shows the inner tube assembly 10 of the catheter 1. This assembly is not visible in FIG. 1. The inner tube assembly 10 includes a tube 14 that fits into the catheter sleeve 3 from the proximal end through one of the fluid fittings 5a, 5b or 5c. The tube assembly 10 may be inserted towards the distal end fully until it stops by the stop block 11 against the catheter tip 2 near the distal end, or a distance further away from the distal end by manual means if so desired. The inner assembly includes generally radial light sources 13 inside at one area of catheter length direction, or in multiple catheter length direction areas, exemplified by light sources 13a, 13b. It is also possible to have the light sources covering the entire length of the catheter or to combine several different type light sources in one area. In order to provide treatment or antimicrobial light radiation, the tube 14 is translucent at least at the locations of light sources 13. At the distal end of the inner tube assembly 10 and near or inside the stop block 11, is an optional vision and illumination system 20 with a field of view 21 in generally the axial forward direction as exemplified here, but it may also be rotated for radial view. It is noted that the inner tube assembly 10 may be made of a material with higher stiffness than the catheter sleeve 3 to provide adequate pushing force with little compression or buckling, and catheter 1 may be made very flexible, to provide ease of insertion and removal of the catheter 1 and patient comfort due to catheter sleeve 3 softness. Also, the inner tube assembly 10 may be easily changed out to a different type or unit while the sleeve 3 remains in the patient. The sleeve 3 may also be left alone in the patient, providing only fluid flow capability with the benefit of low weight, and softness and comfort for the patient. Another aspect of the inner tube assembly 10 is that it may be inserted at different distances ahead of the stop to change the longitudinal emission location of light energy 6 versus sleeve 3.

Figure 3:
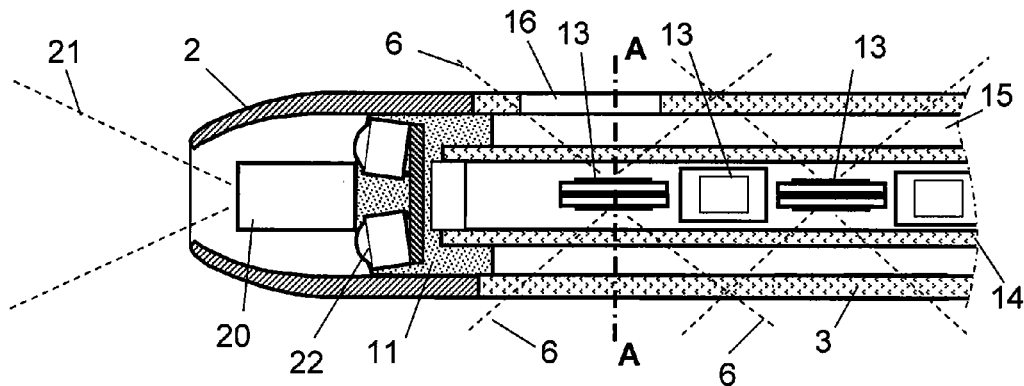
FIG. 3 shows a longitudinal cross-section at the tip at the distal end of a first implementation of the catheter including a camera based imaging system at the tip and treatment or antimicrobial light sources integrated inside the catheter.

FIG. 3 shows a close-up length direction cross-section of the catheter distal area for one implementation example. The tip 2 has smooth exterior shape and serves for insertion of the catheter in the patient and the tip may additionally serve as a stop for stop block 11 near the distal end of the inner assembly 10. For utilization during prostatectomy anastomosis or similar surgery, the tip 2 is preferably made of a hard material and/or coated with a hard surface to prevent suturing needles from penetrating, which could result in false suturing into the catheter tip. The catheter sleeve 3 and the tube 14 inside the sleeve 3 are translucent, permitting light energy 6 to reach the patient. The tip 2 may include a camera or other vision device 20 with vision illumination sources 22; for example as specified in PCT/US12/40877.

Furthermore in FIG. 3, one or more light sources 13 for patient light treatment or antimicrobial use are located in the tube 14. Treatment or antimicrobial light source arrangements are known from prior art, but none of the prior art is suitable for the interior extremely narrow confines of a urinary catheter while simultaneously providing fluid passages which is required by an urinary catheter, and furthermore with provision for catheter vision. Due to recent developments for smart phones and similar hand held devices, there is today available paper thin Light Emitting Diodes (LEDs) with 1 mm and smaller component outline. These may be mounted back to back within the tight catheter confines to provide radiation in opposite directions as illustrated by the different rays of light energy 6.

Furthermore in FIG. 3, the tube 14 is smaller in outer diameter than the inner diameter of the sleeve 3, creating an annular channel 15 for fluid flow, typically flowing in direction from the patient. Fluid flow to the patient for irrigation, cooling or medication purposes may pass through the inside of tube 14. The light sources 13 and associated wiring are preferably coated with an insulating transparent film to prevent electric conduction to the liquid. Also, stop block 11 may includes fluid passage from the inside of the tube 14 to the interior of the tip 2 and to the patient, for instance as shown in PCT/US12/40877. Return flow from the patient may enter the sleeve through a radial opening 16 in the sleeve 3 to flow inside the annular channel 15. Any flow inside tube 8 or annular channel 15 may also have reversed direction or utilized in parallel in both channels for one common flow as needed. In a case where the light sources 13 have high heat dissipation and utilized at a high duty cycle for long times, a small trickle flow through tube 14 is beneficial for avoiding temperature rise inside tube 14. It is noted that with low level light treatment, light sources very close to the patient's tissue due to small dimensions of the catheter, and with intermittent pulsed electric delivery system, high heat dissipation is not expected to be a problem in most situations.

The overall device arrangement in the implementation of FIG. 3 is pointed out since it uses the space available on the proximal side of the camera for a different purpose, specifically achieving radial light treatment or antimicrobial use, combined with fluid flow and catheter vision; all inside a small diameter envelope. The camera wires can be extremely small and do not consume much of the room inside the catheter on the proximal side of the camera. This is one example of a unique added value which is achieved by a device combining the prior disclosed invention in PCT/US12/40877, with the current invention for radial light treatment or antimicrobial purposes.

Figure 4:
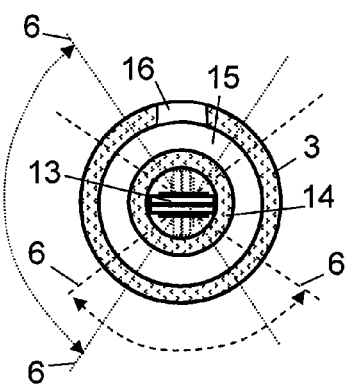
FIG. 4 shows cross-section perpendicular to the length direction of the catheter at section A-A as designated in FIG. 3.

FIG. 4 shows a perpendicular cross-section of the catheter area in FIG. 3 at the annotation A-A. This illustration is visualizing an alternating direction horizontal and vertical light sources 13 providing different angle light energy 6.

Figure 5:
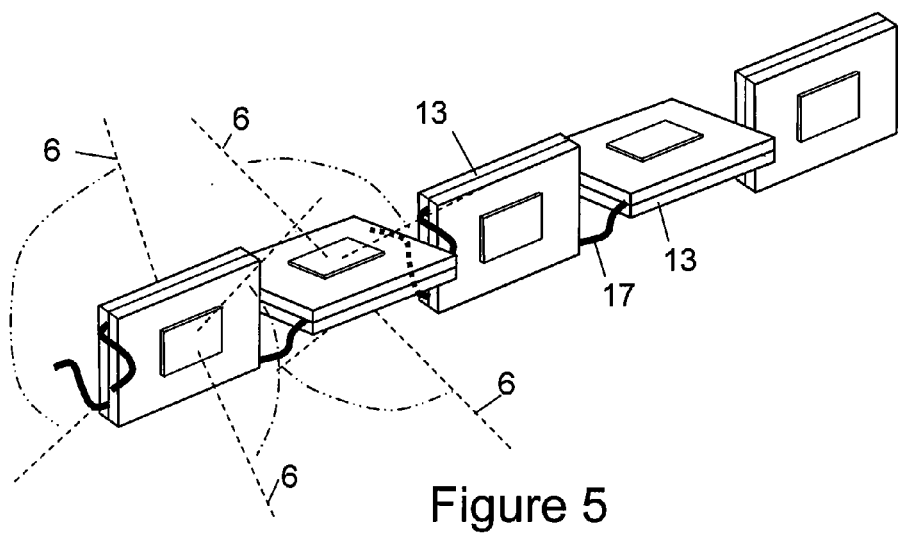
FIG. 5 shows a three-dimensional view of one implementation of the treatment or antimicrobial light source system that is shown two-dimensional in FIG. 3 and FIG. 4.

FIG. 5 shows a perspective view of one embodiment of how to mount light sources 13. The light sources 13 are mounted back to back and in alternating 90 degree orientation, with pairs of sources emitting 180 degrees apart at each source location. The pairs of sources may be mounted on each side of a flexible circuit board 17 with two separate legs, or two separate wires, and sufficient length to make a 90 degree bend between neighboring light sources 13. An unexpected result that is noticed for folding the flex circuit board legs 17 for the 90 degree source alternating pattern, is significantly improved multi axis flex properties of the electric assembly.

Figure 6:
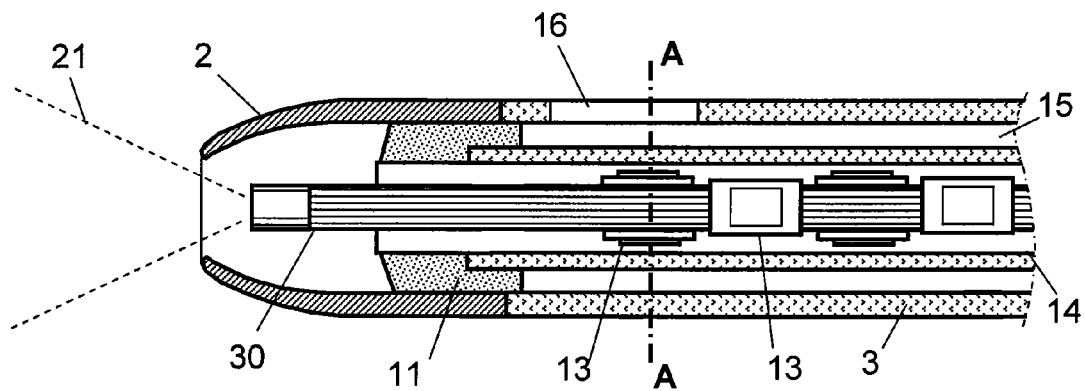
FIG. 6 shows a longitudinal cross-section near the tip section of a second embodiment of the catheter including treatment or antimicrobial light sources and a fiber optics coupled remote imaging system.

FIG. 6 shows an alternate embodiment of illumination and vision. A vision and local image illumination fiber optic bundle (visual guide) 30 provides the vision. For similar fiber optics catheter vision applications, please see patents U.S. Pat. Nos. 6,994,667 and 6,599,237. The visual guide 30 is arranged in the center of tube 14 and surrounded by pairs of 180 degree direction light sources 13, arranged outside the visual guide 30 and inside the tube 14, while rotated 90 degree between pairs.

Figure 7:
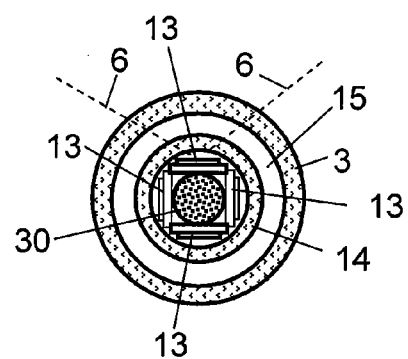
FIG. 7 shows cross-section perpendicular to the length direction of the catheter as designated in FIG. 6.

In FIG. 7 is shown a cross-section perpendicular to the catheter at A-A in FIG. 6. For simplicity, only one of the sets of radiated light energy 6 is shown. For the benefit of manufacturing friendly methods, the tube 14 may initially be a translucent flat sheet where light sources are mounted with apertures against this sheet. Folding this sheet 360 degrees around the visual guide 30 and gluing the resulting longitudinal seam completes the assembly, creating tube 14 with internal light sources 13 and visual guide 30.

Figure 8:
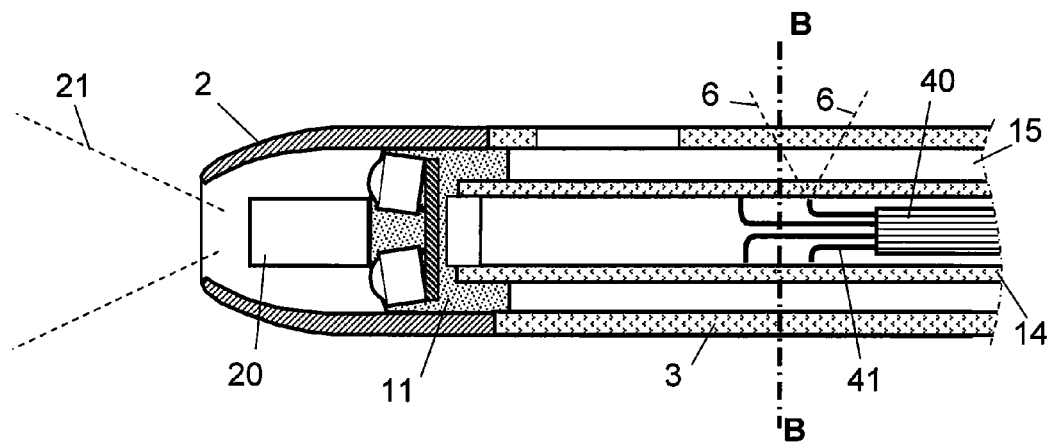
FIG. 8 shows a longitudinal cross-section near the tip section of one different implementation of the assembled catheter including a camera based imaging system at the tip and fiber optics coupled remote treatment or antimicrobial light sources.

FIG. 8 shows yet another embodiment. The vision device 20 is similar as shown in FIG. 3. The light energy delivery for treatment or antimicrobial use is however different. A fiber optics bundle 40 receives light energy from a remote source, or combination of sources, at the proximal end of the catheter. The distal end of the longitudinal fiber optics bundle 40 includes separation of individual fibers, or groups of fibers, into multiple branches 41 with a generally radial direction at different angles. This creates radial light energy 6 for patient treatment or antimicrobial use, in this figure only shown for one of the branches for simplicity.

The overall arrangement in the implementation of FIG. 8 is pointed out since it uses the space available on the proximal side of the camera for a different purpose, specifically achieving radial light treatment, combined with fluid flow and catheter vision; all in a small dimension envelope. The camera wires can be extremely small and do not consume much of the room behind the camera on the proximal side. This is one example of a unique added value which is achieved by combining the prior disclosed invention in PCT/US12/40877, with the current invention for light treatment for healing or antimicrobial purposes.

Figure 9:
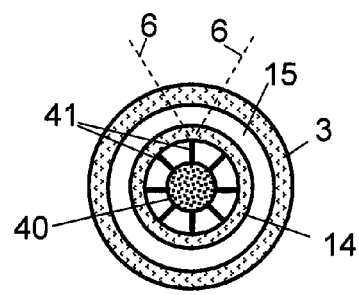
FIG. 9 shows cross-section perpendicular to the length direction of the catheter as designated in FIG. 8.

FIG. 9 is a perpendicular cross-section of the catheter at B-B in FIG. 8, showing one embodiment example of arrangement of the fiber branches 41 in different radial directions to cover 360 degree circumference, and illustrates the annular flow channel 42 created between the inside of tube 14 and fiber optics bundle 40.

Figure 10:
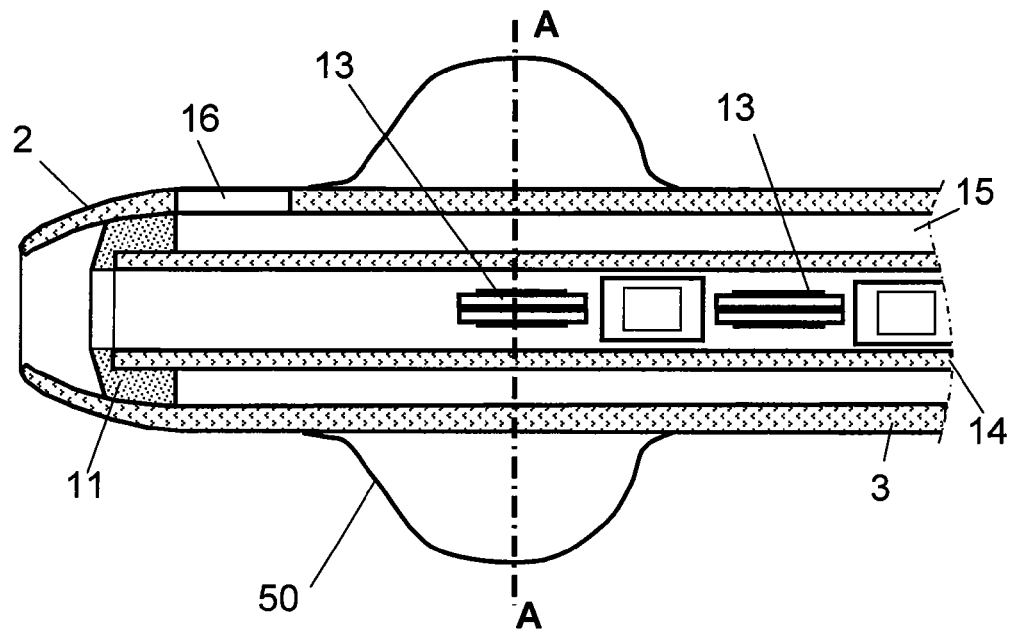
FIG. 10 shows an example of yet another different implementation of the assembled catheter with a balloon near the tip and no imaging system present.

FIG. 10 shows one embodiment of a catheter according to the invention with the configuration change of adding a retention balloon 50, typically near the tip of the catheter. It also shows a second configuration change to the catheter by not including a vision device. Both these configuration changes can be achieved from any of the prior mentioned catheter embodiments. Addition/exclusion of balloon and addition/exclusion of vision are independent and may be done together or individually.

Figure 11:
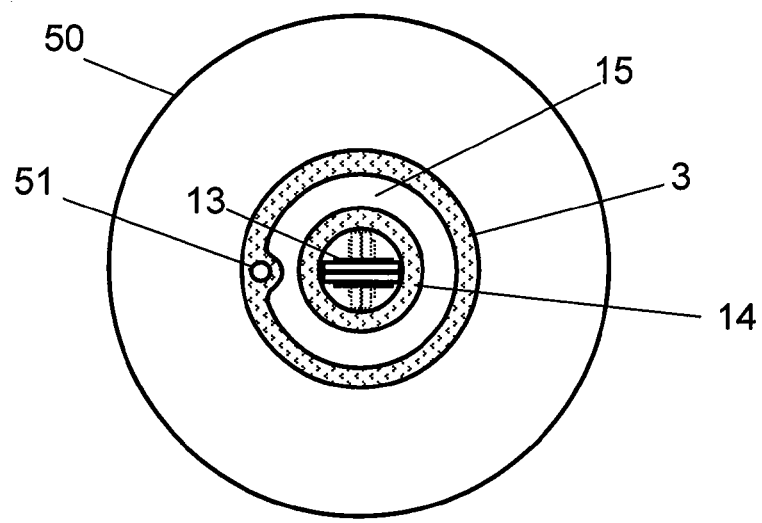
FIG. 11 shows cross-section perpendicular to the length direction of the catheter as designated in FIG. 10.

FIG. 11 shows a perpendicular cross-section across the catheter balloon area at location A-A in FIG. 10. The light sources 13 are arranged similar to the embodiment of FIGS. 3 and 4 in the tube 14. A balloon inflation lumen 51 is added to the catheter sleeve 3 and communicates with balloon 50 to enable the balloon to expand or contract as known by prior art. It is pointed out that the overall assembly may have look-alike appearance with the classic Foley catheter in 3-way configuration—but also offers a unique added value by internal light treatment for healing or antimicrobial action for the patient. It can also add more benefits by the removable inner tube assembly for improved catheter insertion and removal, combined with patient comfort.

FIG. 12a through 12f shows a simplified step by step process for utilization sequence of the invention catheter for a radical prostatectomy and the included urethral anastomosis. Although this is illustrated as one example of utilization of the invention catheter, it is emphasized that similar or different utilization sequences may be beneficial for other internal medical procedures involving combined requirements for light energy for treatment, fluid handling, and vision. The sequence starts in FIG. 12a and ends at 12f, in alphabetic order.

FIG. 12a shows schematically the invention catheter 1, bladder 60, prostate gland 61 and urethra 62. In this view, vision illumination is enabled and catheter 1 is utilized to inspect the urethral interior before proceeding with incision points 63 to remove the prostate.

FIG. 12b shows both the forward axial vision illumination 21 in the catheter 1 and treatment light energy 6 are enabled and radiate through the thinner portions of tissue to become visible for the operator. This assists the operator to properly locate the incision points 63 for urethral removal, which is particular useful during a laparoscopic surgery procedure to provide visibility internal to the body. The catheter is retracted from the incision point while incision is made but the catheter forward vision can with benefit illuminate the incision areas similar as in FIG. 12a.

FIG. 12c shows the prostate gland removed and start of sutures on the bladder urethral stump. The catheter vision and related illumination 21 will aid in placing these sutures properly. After this, catheter is retracted some distance to allow completion of the sutures to the urethra side and related stretching of the bladder.

FIG. 12d shows sutures completed to both the bladder stump and the urethra, after the parts have been pulled together for close fit. The catheter 1 is now utilized to inspect the anastomosis from the inside, as well as providing illumination visible from the outside for alerting operator for potential anastomosis gaps that must be tightened.

FIG. 12e shows the catheter advanced for healing treatment light 6 directed from inside to the urethral anastomosis area. This may be started immediately after sutures are complete which aids faster start of the healing process. The healing light energy may be red or infrared for deep penetration, or selected in spectrum towards the green or blue for more surface effect. The healing light may be advantageously operated in pulsed mode, since some healing effects on living cells have been shown to improve by properly pulsed light. This pulsed operation also reduces heat generation. Since there is a very short distance between the light sources inside the treatment catheter 1 and the tissue inside the urethra, the average power can be kept relatively low to deliver desired treatment effect. It is of interest to note that the anastomosis healing process for a severed urethra must be especially well controlled at the thin inside mucosa linings that are joined between the urethra and bladder stump, but is more forgiving for the surrounding muscle layers. The invention catheter delivers light treatment from the inside directly to the internal mucosa lining and is therefore a unique solution for improved healing process.

FIG. 12f shows a short-term or long-term post-surgery application of a catheter 1 with retention balloon 50 and including delivery of healing light energy 6 for completion of accelerated healing of the anastomosis while still providing traditional Foley catheter functionality.

Figure 13:
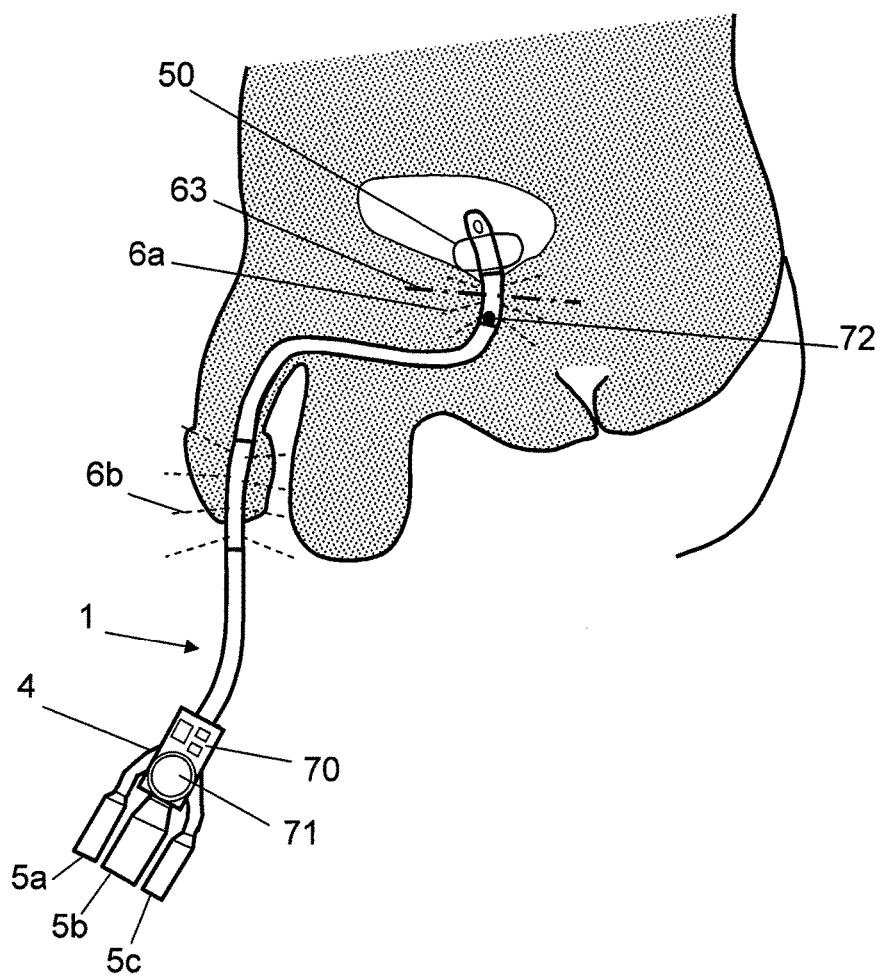
FIG. 13 shows a male anatomy lengthwise cross-section with the catheter system applied for treatment for extended time of use while reducing infection risk.

FIGS. 13 (male anatomy) and 14 (female anatomy) show another aspect of the invention catheter applied for long term catherization of patients while providing antimicrobial features for reduced urinary tract infection risk. In FIG. 13, it is shown simultaneous healing treatment and antimicrobial features.

FIG. 13 shows a catheter 1 applied to a male patient, for example for post-surgery treatment. The catheter 1 provides conventional Foley functionality as well as light treatment for healing and antimicrobial light treatment features. The catheter delivers light energy 6a to the urethral anastomosis line or other part needing healing at a treatment area 63, and different light energy 6b for antimicrobial features outside and inside the urethral meatus and part of the urethra.

The catheter 1 has a small electric energy source 70, here shown mounted on the catheter manifold 4, or it may alternatively be integrated in the manifold molding. The electric energy source may have an integrated battery 71 and the source may be powered or charged via a remote electric low voltage, low power source. The electric energy source has the function of timely activating or pulsing light energy 6a for healing treatment after surgery, and light energy 6b for antimicrobial features. The electric energy source 70 may also furnish visual or audible indicators and alarms for proper operation of the light energies 6a and 6b. In this application of the invention, integrated vision for long term internal observation is typically not necessary. A small and low-cost sensing device, for instance an internal temperature sensor 72 may be included in the catheter and monitored for proper results by the electric energy source 70.

The treatment feature in FIG. 13 functions as follows. The patient treatment zone 63 is periodically exposed from the catheter to low level visible or IR light energy 6a, for surgery healing purposes, reduction of scar tissue, or treatment of a diseased area. This invention assists to achieve quicker and more effective healing by beneficial tissue healing and growth influence by light.

The antimicrobial feature in FIG. 13 functions as follows. The meatus and urethral antimicrobial treatment zone is periodically exposed from the inside by low level UV, blue, or other light energy 6b. It has been proven that this type of low level energy can be effective for killing of bacteria and reducing microbial growth rate. This light creates an antimicrobial barrier zone in the small gap between the catheter and the urethral wall, as well for the fluid channels inside the catheter. The antimicrobial barrier zone will aid to reduce migration of bacteria from the exterior of the patient into the urinary tract and biofilm buildup on the catheter, where a spreading infection may result in poor outcome, need for extensive corrective procedures, and reduced quality of life for the patient.

This application of the invention in FIG. 13 provides good patient comfort which is of value particularly if the catheter may need to dwell in the patient for days or weeks. The light weight, flexibility, and freedom from plurality of cables or tubes connected to separate external instruments are part of the patient comfort.

Figure 14:
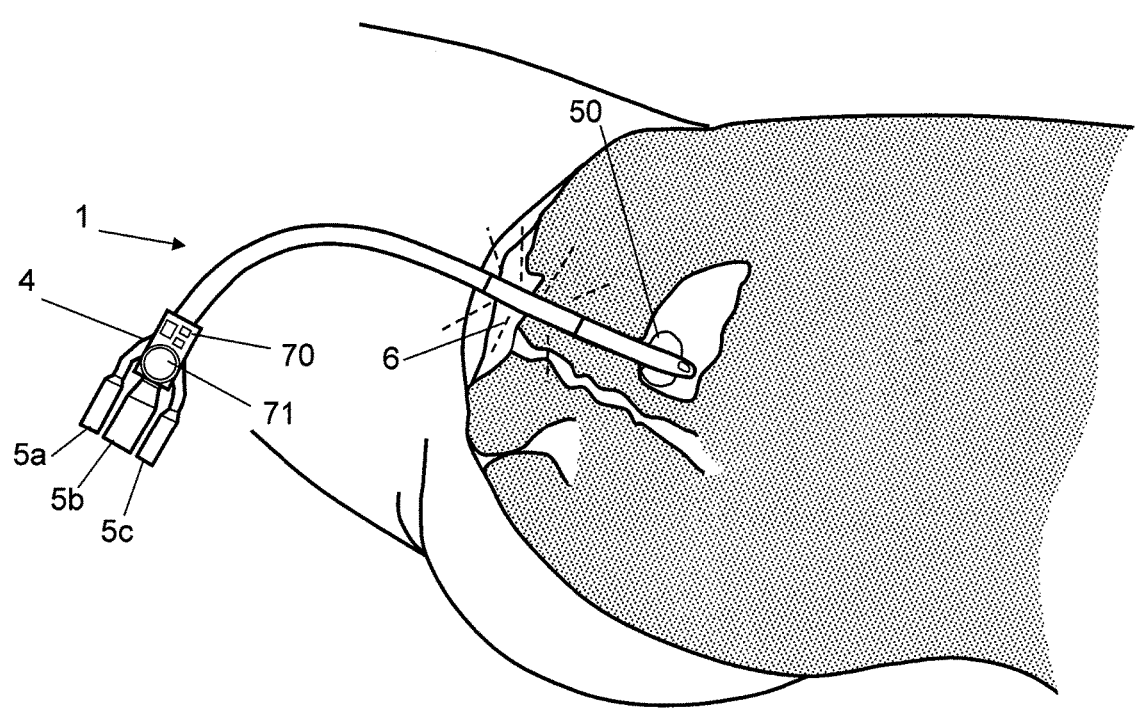
FIG. 14 shows a female anatomy lengthwise cross-section with the catheter system applied for extended time of use while reducing infection risk.

FIG. 14 shows an example of female applications of the invention. The catheter in this example provides traditional Foley capability as well as an antimicrobial feature. It is noted that a light healing or treatment feature similar to what is described in FIG. 13 may also be added. In the example of FIG. 14, there is shown only a light based antimicrobial feature utilizing light 6 in a similar way as part of the description of FIG. 13. This antimicrobial zone may start from outside the urethral meatus and continues a desired distance inwards the urethra or all the way into the bladder.

It is noted that the female applications of the invention catheter in FIG. 14 may also include healing or treatment light similar to FIG. 13.

For a female catherization as illustrated schematically in FIG. 14, it is noted that vaginal vault bacteria or bacteria from nearby anus area, may migrate and deposit near the catheter entry into the urethral meatus, and then attempt to migrate inward along the urethra in the narrow gap between catheter exterior and urethral interior. Due to the short urethra of a female, and if the catherization is performed without an effective antimicrobial barrier, such migrated bacteria may spread into the rest of the urinary tract, causing possibly serious infections. This invention reduces infection risk by the novel integration of antimicrobial lights in the catheter.

Figure 15:
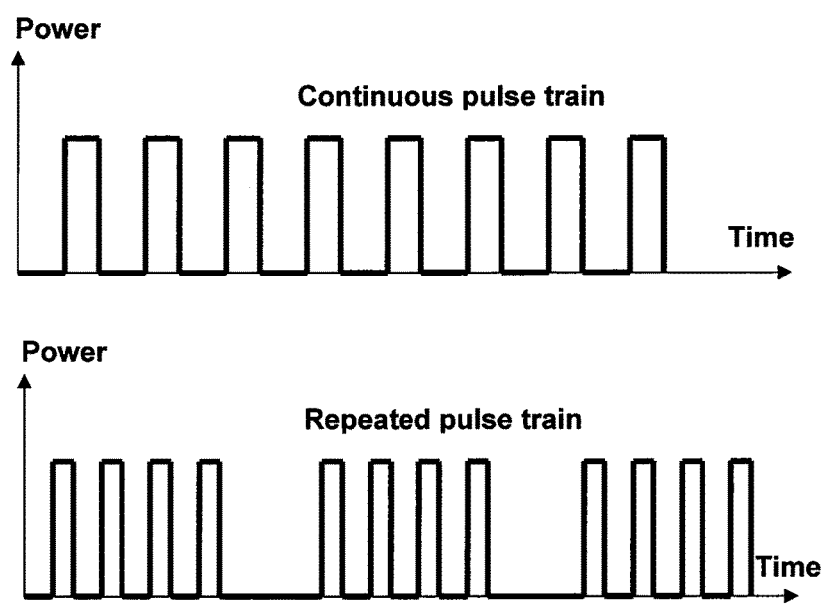
FIG. 15 shows an example of how the treatment energy can be pulsed for maximizing effect on treated tissue.

FIG. 15 illustrates how the treatment sources may be pulsed for increasing treatment effect to the cells, while also reducing light source power consumption and heat generation in the catheter. It is known that living cells can react differently to pulsed radiant energy than to continuous exposure. Treatment results for properly pulsed energy can be improved versus continuously applied energy. The pulsed energy may be applied in an extended duration pulse train with an on time and duty cycle, or by periodically repeated pulse train, each with a finite number of pulses. Pulse length for tissue healing treatment may, for instance, be in the range 1 μs to 1 ms, and overall power duty cycle 1% to 50%, however, this is highly dependent on wavelength, peak power and allocated time for a full medical procedure.

Variations of the invention will be apparent to the skilled artisan.

The invention claimed is:

1. A catheter comprising an outer translucent catheter sleeve having a proximal end and a distal end; a vision and illumination device positioned in or at a distal end of the sleeve for viewing an interior of the patient; a translucent tube, narrower in diameter than a diameter of the sleeve, positioned within the outer sleeve such that the translucent tube extends substantially from the proximal end to the distal end of the outer sleeve, and the translucent tube being insertable and removable from a proximal end of the catheter; at least one medicinal radiant energy source configured to emit medicinal radiant energy to the patient with an irradiance of 0.1-200 mW/cm$^2$ at wavelengths of 450-1000 nm for healing treatment or 350-600 nm for antimicrobial treatment, positioned within said translucent tube for transmitting said medicinal radiant energy transversely through the translucent tube and transversely through the translucent sleeve into the interior of the patient for treating interior tissue cells of the patient; and a fluid channel, for passing a fluid to or from the patient, formed between said tube and said sleeve;

wherein the vision and illumination device, the translucent tube, and the at least one medicinal radiant energy source form an inner assembly, which is insertable and removable from the proximal end of the outer sleeve; and wherein, after the inner assembly is removed from the proximal end of the outer sleeve, the outer sleeve is adapted to function as a conventional fluid flow catheter.

2. The catheter of claim 1 wherein the at least one medicinal radiant energy source comprises a plurality of light sources configured to emit medicinal radiant energy.

3. The catheter of claim 2 wherein the light sources are selected from the group consisting of light emitting diodes, laser diodes, organic light emitting diodes and fiber optic bundles.

4. The catheter of claim 1 wherein the translucent tube functions as a second fluid channel.

5. The catheter of claim 1 wherein the vision device is a camera or a fiber optics imaging system.

6. The catheter of claim 1 wherein the radiant energy source is configured to emit medicinal radiant energy in a dose effective for providing a direct medicinal benefit to the interior treated tissue cells of the patient.

7. The catheter of claim 1 wherein the radiant energy source is configured to emit medicinal radiant energy in a dose effective for directly promoting healing of or providing a direct antimicrobial effect to the interior treated tissue cells of the patient and/or the catheter.

8. The catheter of claim 1 wherein the at least one radiant energy source is configured to emit radiant energy in a pulsed mode.

\* \* \* \* \*